United States Patent
Seeley et al.

(10) Patent No.: US 9,320,571 B2
(45) Date of Patent: Apr. 26, 2016

(54) LEAD TRACKING AND POSITIONING SYSTEM AND METHOD

(75) Inventors: Dale F. Seeley, Spring Park, MN (US); Phillip Falkner, Minneapolis, MN (US); Michael Hegland, Mounds View, MN (US); Steven L. Hartmann, Superior, CO (US); Brad Jacobsen, Erie, CO (US)

(73) Assignee: Medtronic, Inc., Minneapolis, MN (US)

( * ) Notice: Subject to any disclaimer, the term of this patent is extended or adjusted under 35 U.S.C. 154(b) by 1415 days.

(21) Appl. No.: 12/649,932

(22) Filed: Dec. 30, 2009

(65) Prior Publication Data

US 2011/0160568 A1 Jun. 30, 2011

(51) Int. Cl.
*A61B 5/05* (2006.01)
*A61B 19/00* (2006.01)

(52) U.S. Cl.
CPC ..... *A61B 19/5244* (2013.01); *A61B 2019/4857* (2013.01); *A61B 2019/5251* (2013.01); *A61B 2019/5272* (2013.01)

(58) Field of Classification Search
CPC ......... A61N 1/04; A61N 1/05; A61N 1/0551; A61B 19/5244; A61B 2019/5251
See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 5,983,126 A | 11/1999 | Wittkampf | |
| 6,474,341 B1 | 11/2002 | Hunter et al. | |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 6,714,823 B1* | 3/2004 | De Lurgio et al. | 607/122 |
| 6,973,352 B1* | 12/2005 | Tsutsui et al. | 607/122 |
| 7,313,430 B2 | 12/2007 | Urquhart et al. | |
| 7,366,562 B2 | 4/2008 | Dukesherer et al. | |
| 2003/0114752 A1 | 6/2003 | Henderson et al. | |
| 2004/0097806 A1* | 5/2004 | Hunter et al. | 600/434 |
| 2004/0143197 A1* | 7/2004 | Soukup et al. | 600/585 |
| 2005/0049486 A1* | 3/2005 | Urquhart et al. | 600/429 |
| 2005/0085714 A1 | 4/2005 | Foley et al. | |
| 2005/0085720 A1 | 4/2005 | Jascob et al. | |
| 2006/0025677 A1 | 2/2006 | Verard et al. | |
| 2007/0164900 A1* | 7/2007 | Schneider et al. | 342/357.12 |
| 2008/0039738 A1 | 2/2008 | Dinsmoor et al. | |
| 2008/0064947 A1 | 3/2008 | Heruth et al. | |
| 2008/0071170 A1 | 3/2008 | Kenneth | |
| 2008/0171934 A1* | 7/2008 | Greenan et al. | 600/411 |
| 2008/0255446 A1 | 10/2008 | Akins | |
| 2009/0275956 A1 | 11/2009 | Burnes et al. | |
| 2010/0036227 A1* | 2/2010 | Cox et al. | 600/374 |

OTHER PUBLICATIONS

International Search Report and Written Opinion mailed Jan. 28, 2011 claiming benefit of U.S. Appl. No. 12/649,932, filed Dec. 30, 2009.
Foley, "The StealthStation: Three-Dimensional Image-Interactive Guidance for the Spine Surgeon," Spinal Frontiers, Apr. 1996, pp. 7-9.

* cited by examiner

*Primary Examiner* — Amanda Lauritzen Moher
*Assistant Examiner* — Serkan Akar
(74) *Attorney, Agent, or Firm* — Harness, Dickey & Pierce, P.L.C.

(57) ABSTRACT

Image data can be obtained with an imaging device. A location of the imaging device relative to a subject can be determined. A location of an instrument can be tracked relative to the subject using a tracking system. Also, the tracked location of the instrument can be illustrated relative to the image data.

30 Claims, 5 Drawing Sheets

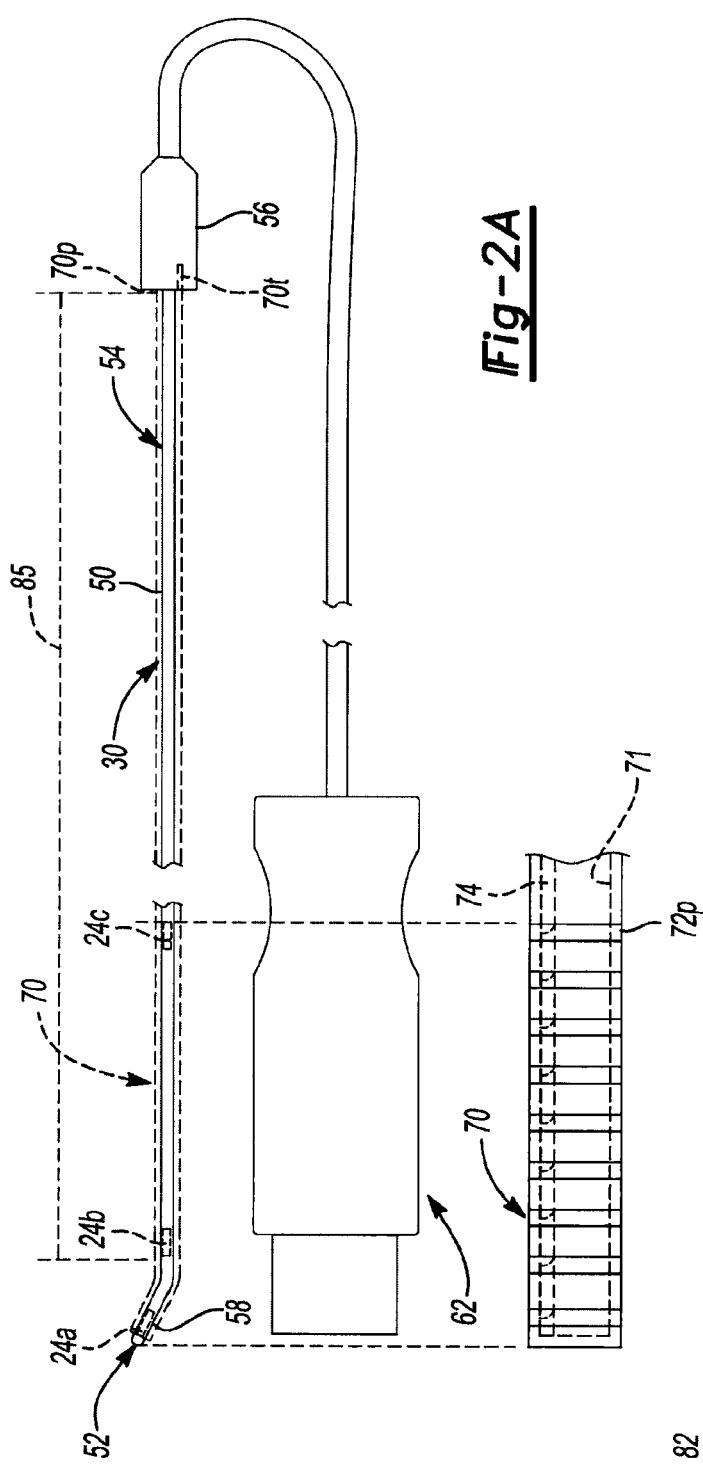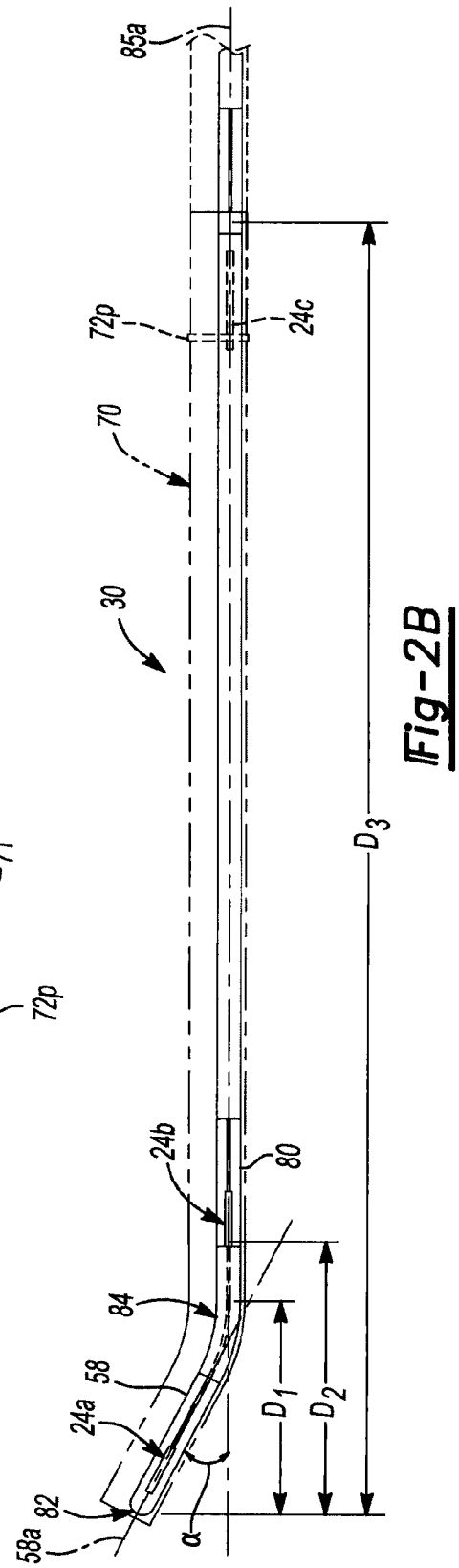

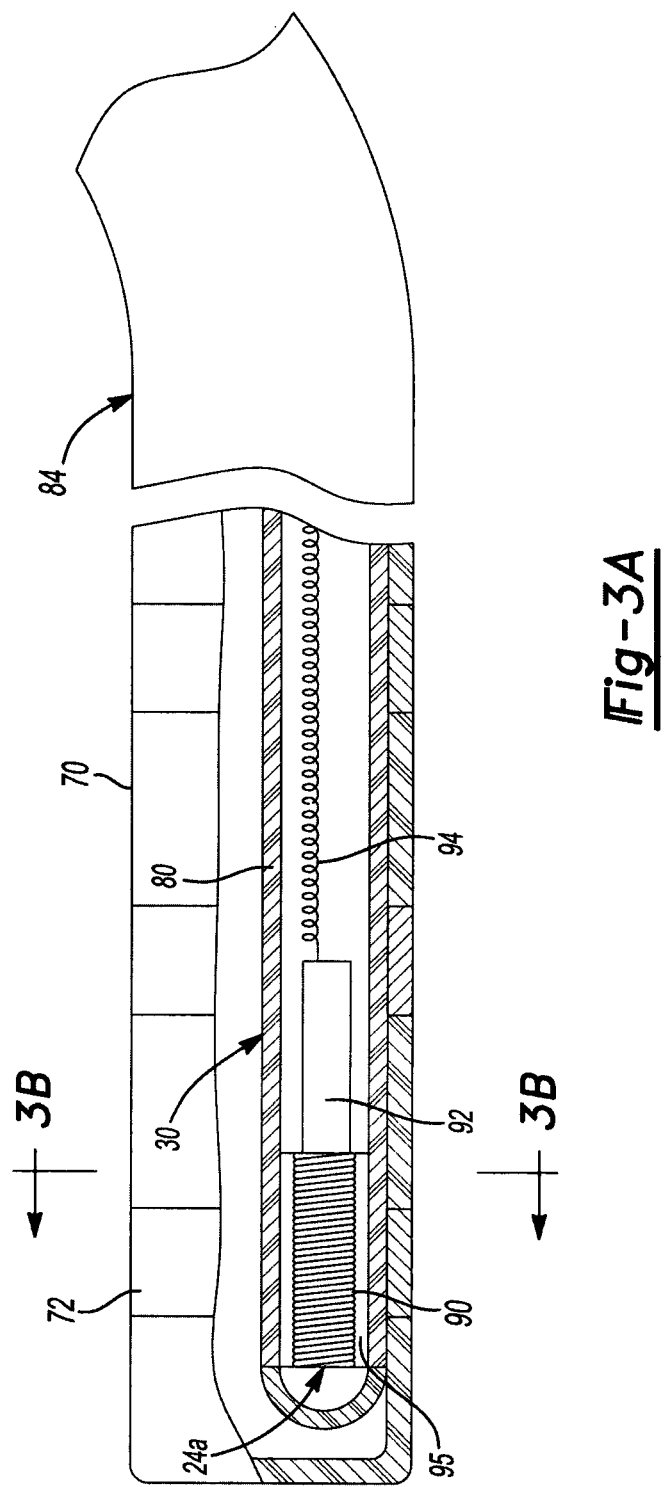

LEAD TRACKING AND POSITIONING SYSTEM AND METHOD

FIELD

The present disclosure relates generally to navigated surgery, and more specifically, to a method and apparatus for performing a surgical procedure with the use of multiple tracking devices to determine the location of a single instrument.

BACKGROUND

Image guided procedures, such as surgical procedures, can utilize image data obtained prior to or during a medical procedure to assist a user, such as a surgeon, in performing and navigating a procedure. Such procedures can be referred to as navigated, guided, or computer assisted surgery procedures. Recent advances in imaging technology, especially in imaging technologies that produce high-detailed, two, three, and four dimensional image data (e.g. computed tomography (CT), magnetic resonance imaging (MRI), fluoroscopic imaging (such as with a C-arm device), positron emission tomography (PET), and ultrasound (US) imaging) has increased the interest in navigated surgical procedures.

In one example, navigation systems can include tracking systems to track the location of tracking devices associated with an instrument. The tracking system can determine the location of the tracking device and calculate a location of a portion of the instrument based on the tracked location of the tracking device. The navigation system can illustrate a position and display it on the image data.

SUMMARY

An instrument can be tracked during an operative procedure. The instrument can be illustrated as an icon or representation superimposed on acquired image data to identify the position of the instrument relative to a patient or subject space. To allow for navigation, the instrument may include a tracking device. The tracking device can include a trackable portion, such as a conductive coil that can be detected by a suitable tracking system. The tracking device can also include more than one tracking device all associated with each other and in a single instrument.

A dynamic reference frame (DRF) can also be used by the tracking system to maintain a registration or localization of the patient space to the image space. The DRF can include an appropriate tracking device that is fixed to a portion of the patient that allows the tracking system to determine whether the patient has moved and to where. Tracking patient movement with the DRF can allow registration to image space to be maintained during a procedure.

According to various embodiments, a lead placement system for placing a lead in a subject is disclosed. The lead placement system can include a stylet including a stylet tube formed by a stylet wall encompassing a stylet internal volume, the stylet tube having a stylet body extending along a first axis between a stylet proximal end and a curved portion, the stylet tube further having an angled portion extending along a second axis from the curved portion to a stylet distal end. A first tracking device can be positioned within the internal stylet volume of the stylet at the angled portion and a second tracking device can also be positioned within the internal stylet volume of the stylet proximal to the curved portion of the stylet. The stylet is operable to be positioned within an internal lead volume of the lead to move the lead into the subject.

According to various embodiments, a lead placement system for placing a lead in a subject is disclosed. The lead placement system can include a trackable stylet including a stylet tube formed by a stylet wall encompassing a stylet internal volume, the stylet tube having a stylet body extending along a first axis between a stylet proximal end and a curved portion, the stylet tube further having an angled portion extending along a second axis from the curved portion to a stylet distal end. The system can further include a tracking system including a first tracking device positioned within the internal stylet volume of the stylet at the angled portion, such as at or adjacent the tip, a second tracking device positioned within the internal stylet volume of the stylet proximal a curved portion of the stylet; and a third tracking device positioned within the internal stylet volume and proximal to the second tracking device. The tracking system is operable to track all of the first tracking device, the second tracking device, and the third tracking device. A lead, which includes a lead wall extending along a longitudinal lead axis and defining an internal lead volume, can be positioned over the stylet so that the stylet is positioned within the internal lead volume and the third tracking device is positioned relative to a portion of the lead. For example, the third tracking device can be positioned near a proximal lead electrode. A display device can display an image and an icon representing a location of at least a portion of the trackable stylet, the lead, or combinations thereof. The trackable stylet is operable to be positioned within the internal lead volume of the lead to move the lead into the subject.

According to various embodiments, a method of placing a lead in a subject is disclosed. The method can include positioning a trackable stylet including a stylet tube formed by a stylet wall encompassing a stylet internal volume, the stylet tube having a stylet body extending along a first axis between a stylet proximal end and a curved portion, the stylet tube further having an angled portion extending along a second axis from the curved portion to a stylet distal end. A first tracking device positioned within the internal stylet volume at an angled portion of the trackable stylet that is distal to a curved portion of the trackable stylet and a second tracking device positioned within the internal stylet volume positioned in a stylet body proximal to the curved portion of the stylet can both be tracked. A lead can be moved within a subject and an icon representing a position of at least one of the trackable stylet and the lead can be displayed.

BRIEF DESCRIPTION OF THE DRAWINGS

The present teachings will become more fully understood from the detailed description and the accompanying drawings, wherein:

FIG. 2A is a plan view of a stylet and lead;

FIG. 2B is a detailed view and partial cross-section view of the stylet;

FIG. 3A is a detailed cross-sectional view of a portion of the stylet and the lead;

DETAILED DESCRIPTION OF VARIOUS EMBODIMENTS

Figure 1:
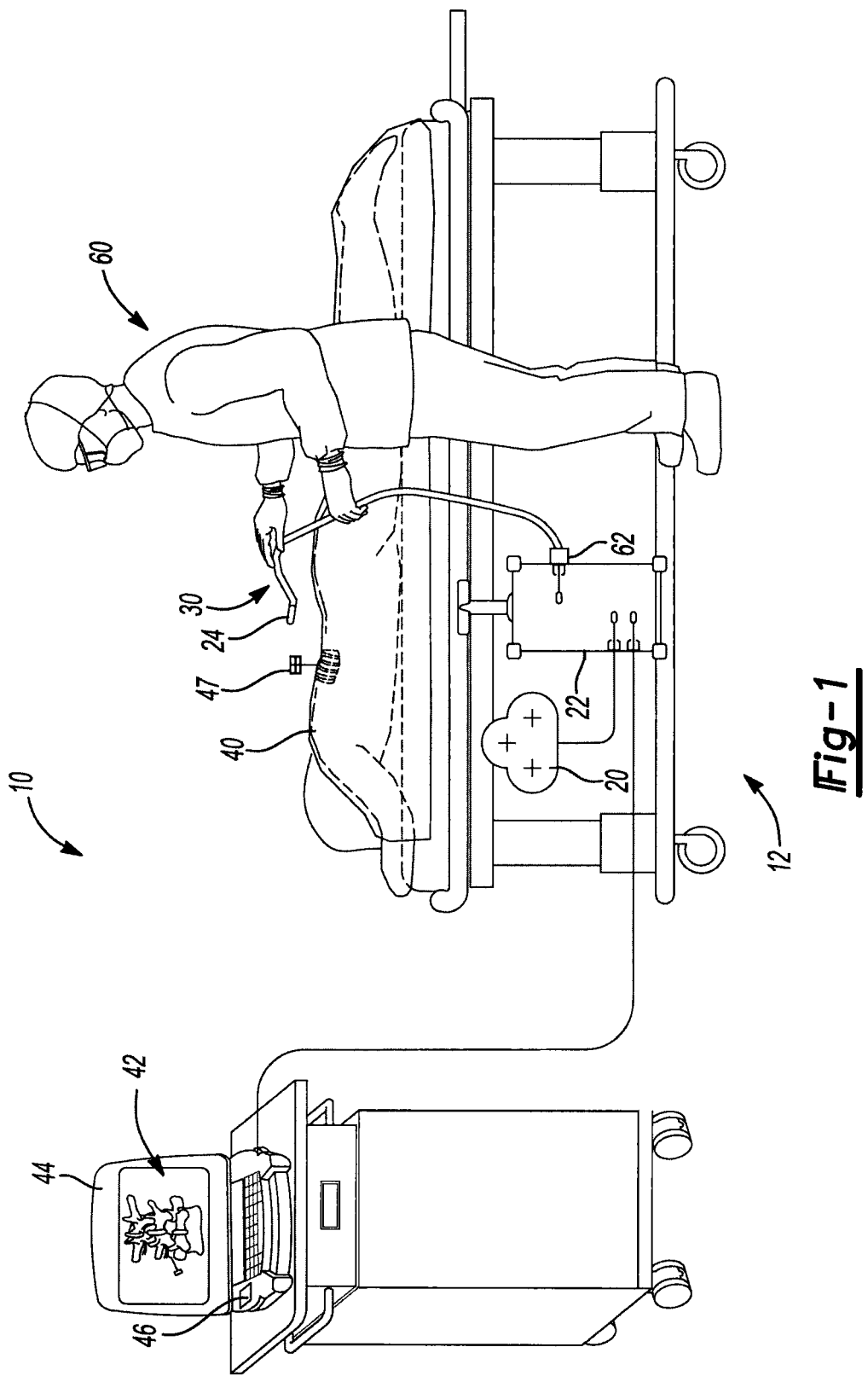
FIG. 1 is a diagram of a navigation system according to various embodiments including an imaging device and tracking system.

The following description of various embodiments is merely exemplary in nature and is in no way intended to limit the teachings, its application, or uses. By way of example, the following description is directed toward a spinal surgical procedure often described as spinal cord stimulation. It is appreciated, however, that the following may be used for other image guided surgeries such as other orthopedic procedures, cardiac procedures, neurological procedures, or any other surgical or medical procedure.

A system is disclosed that includes a stylet 30, such as a hypotube, that can be used to assist in placing a secondary instrument, such as a stimulating lead 70, into a patient 40. The stylet 30 can include one or more tracking devices to track a location of the stylet 30 and the lead 70 when placed over the stylet 30. The stylet 30, as a tube, can include the tracking devices 24 fixed within the tube. Also, the stylet can have a curved portion 84 to allow the stylet 30 to be directed or steered into the patient 40 and the tracking devices 24 can assist in determining the position, including the location and direction of movement, of the stylet 30. The tracking devices 24 can be positioned with the stylet 30 to determine locations of various portions of the lead 70, such as a position of an electrode on a stimulating lead.

FIG. 1 schematically illustrates a navigation system 10 that can include an electromagnetic (EM) tracking system 12. The EM tracking system 12 can include an electromagnetic (EM) localizer 20, which can include a receiver or transmitter coil array having one or more coils. The EM tracking system 12 can also include an EM controller 22 and an EM tracking device 24. It will be understood, as discussed further herein, that multiple EM tracking devices can be provided and tracked with the EM tracking system 12.

The EM controller 22 can control the EM localizer 20 (such as powering and controlling the coil array) and interface with tracking devices 24. The tracking devices 24 can also include one or more coils that operate to transmit or receive an EM field. The tracking devices 24 can be associated or incorporated into an instrument, such as a stylet 30 (discussed in detail herein). The tracking devices 24 associated with the stylet 30 can be used to track and determine a location of the stylet 30 and an associated instrument.

The EM tracking system may be the STEALTHSTATION® AXIEM™ Navigation System, sold by Medtronic Navigation, Inc. having a place of business in Louisville, Colo.; or it can be any EM tracking system such as those described in U.S. patent application Ser. No. 10/941,782, filed Sep. 15, 2004, published as U.S. Pat. App. Pub. No. 2005/0085720, on Apr. 21, 2005, titled "METHOD AND APPARATUS FOR SURGICAL NAVIGATION"; U.S. Pat. No. 5,913,820, titled "Position Location System," issued Jun. 22, 1999; U.S. Pat. No. 5,592,939, titled "Method and System for Navigating a Catheter Probe," issued Jan. 14, 1997; and U.S. Pat. No. 5,983,126, titled "Catheter Location System and Method," issued Nov. 9, 1999, all of which are incorporated herein by reference. It will be understood that the tracking system may also be or include any appropriate non-line of sight tracking system, such as an acoustic, ultrasound, radiation, radar, etc.

Although the details of operation of the EM tracking system 12 are generally known, a summary is provided here for reference. A patient 40 and the physical volume relative to the patient 40 defines a patient or subject space. This is the space or volume in which the instrument 30 can move and can be tracked (when the tracking device is within range of the localizer). Image space is the volume defined by image data of the patient. Image data can be acquired, pre-, post-, or intra-operatively, with any appropriate imaging device, such as a magnetic resonance imaging (MRI) system, computer tomography (CT) imaging system, fluoroscopy, ultrasound, etc., and displayed as an image 42 on a display device 44.

The display device 44 can be associated with a processor system 46, such as a workstation, of the navigation system 10. The processor system 46 can be a single processing core or system that is operable to execute different algorithms relating to image analysis, tracking, etc. or the processing system can be separated into separate processing cores or systems for processing unique tasks. Regardless of the configuration, the display device 44 is operable to illustrate the image 42 based on the image data and other information, as discussed herein.

The transmitter coil array 20 can include a plurality of coils and each can generate selected electromagnetic fields in the subject space. The EM fields in the subject space can also be referred to as navigation fields and be used to define a volume that can be navigated with the navigation system 10. For example, the EM localizer 20 can generate a field near the patient 40 so that it can be used to track the location of the tracking devices, as discussed herein. The navigation field can at least partially overlap the subject space. Discussion herein of patient space will be understood to be a specific example of subject space.

The EM controller 22 can drive each coil in the EM localizer 20 in a time division multiplex or a frequency division multiplex manner. In this regard, each coil may be driven separately at a distinct time or all of the coils may be driven simultaneously with each being driven by a different frequency. Upon driving the coils in the EM localizer 20 with the EM controller 22, electromagnetic fields can be generated which define the navigation field in the subject space.

The electromagnetic fields generated in the patient space can induce currents in the EM tracking device 24 positioned on or in the instrument 30. These induced signals from the EM tracking device 24 can be transmitted to the EM controller 22 and/or the processor 46. The EM controller 22 may also provide all the necessary electrical isolation for the navigation system 10. Alternatively, the electrical isolation may also be provided in a separate device. The EM controller 22 can also include amplifiers, filters, and buffers to directly interface with the EM tracking device 24. Alternatively, the tracking device 24 may employ a wireless communications channel, such as that disclosed in U.S. Pat. No. 6,474,341, entitled "Surgical Communication Power System," issued Nov. 5, 2002, herein incorporated by reference, as opposed to being coupled directly to EM controller 22.

Alternatively, the tracking device 24 can generate a field sensed by the EM localizer 20 to track the tracking device 24. In other words, the tracking device includes one of more coils that can generate EM fields. The EM fields generated by the tracking device 24 can be received or sensed by the coils of the localizer for tracking. Thus, the tracking devices 24 or the EM localizer 20 can received and/or generate the fields.

It will be further understood that the tracking system 12 can be used to track any appropriate instrument relative to any appropriate system, such as tracking an instrument relative to a mechanical system (e.g. aerospace systems, automobile systems, etc.) Tracking the tracking device 24 within the patient 40 is exemplary and intended for discussion of the subject matter disclosed herein. The subject matter disclosed herein, however, can be used in relation to other physical volumes or spaces.

In an image guided or surgical navigation system, image data of the patient 40, or any appropriate subject, can be obtained. The image data can be obtained with appropriate image systems such as magnetic resonance imaging (MRI) system, computed tomography (CT) system, fluoroscopy systems, or other appropriate imaging systems. The image data obtained with the appropriate imaging system can be saved and used by the navigation system 10 for image guided surgical procedures. As illustrated herein, the image data can be displayed as an image 42 on the display device 44.

The image data defines image space, as discussed above. The image space can be registered to the subject space that can be defined by the navigation fields, such as with the localizer 20. According to various embodiments, for example according to the electromagnetic navigation system illustrated in FIG. 1, the localizer 20 generates an EM field as the navigation space. The EM field can be sensed by the tracking devices and the position of the tracking devices can be calculated, as discussed in the references incorporated above. The image space can be registered to the subject space to allow for an accurate illustration of the position of an instrument, such as the stylet 30, relative to the patient 40.

Registration generally occurs by transforming the image space to the subject space by correlating fiducial image data in the image space to fiducial points in the subject space. Fiducial points can be implanted devices, a surface of a subject (such as a skin or bone surface of a patient), anatomical points (such as boney portions), and the like that are identifiable both in the image data and in the subject space. Registration is discussed in more detail in the incorporated references, and is discussed here briefly only for completeness of the current discussion.

Once registration occurs, an illustration of a tracked position of the instrument 30 can be displayed relative to the image 42 on the display device 44. A dynamic reference frame (DRF) or patient tracker 47 can be affixed to the patient 40 to maintain registration. The DRF 47 can be tracked with the tracking system 12 to determine movement of the patient 40. The tracked movement of the patient 40 with the DRF 47 can be used to maintain registration of the image space to the subject space.

Registration can be substantially automatic or require user intervention. Automatic registration can occur, for example, using the imaging system that is in an operating room. User intervention can include identifying both subject space fiducial markers and image space fiducial points.

With reference to FIGS. 2A and 2B, the stylet 30 can include an elongated substantially rigid walled tube 50 that can be formed with a sheet that terminates at a first or distal end 52 and a second or proximal end 54. At or near the proximal end 54 a handle 56 allows a user to orient the stylet 30. Near the distal end 52 can be an angled tip portion 58, as discussed further herein, that extends distally from a curved portion 84. The angled portion can be the tip portion 58 that extends to the distal end 52, but is understood to be a portion that extends along an angled axis 58*a* formed at an angle α to a long body axis 85*a*

The curved portion 84 can be defined by a radius R of about 0.2 inches (in.) (about 5 millimeters (mm)) to about 0.6 in. (about 15 mm). The stylet 30 may also be a solid stylet with tracking devices formed on the exterior of the solid stylet. Such a solid stylet would include the various trackability features as discussed herein.

The handle 56 can allow a user, such as a surgeon 60 to manipulate or orient the stylet 30 by rotating the handle 56 thereby rotating the rigid tube 50. Generally the portion between the handle 56 and the curved portion 84 can be referred to as a stylet body 85. It will be understood that by rotating the handle 56 and the tube 50, respectively, the tip portion 58 of the stylet 30 can be moved relative to the patient 40 to thereby steer a secondary instrument, including a lead 70 (e.g. a stimulator lead), along a desired path and into a desired location. The lead 70 can extend over the stylet 30 and can include a tab 70*t* to engage a bore in the handle 56 to rotationally hold the lead 70 relative to the handle 56.

Extending from the proximal end of the handle 56 can be a connector 62 that connects to the EM controller 22. The connector 62 can be used to transmit or carry a signal to the EM controller 22. The signal can relate to the signal based upon the tracked location or a signal that can be used to determine a location of the stylet 30 based upon one or more tracking devices 24*a*-24*c* (illustrated in FIG. 2B), as discussed further herein.

With continuing reference to FIG. 2A, the stimulating electrode lead or other secondary instrument 70 can be positioned relative to the stylet 30, as discussed further herein. For example, the stylet 30 can be placed in a bore or passage defined by an internal wall surface 71 of the lead 70. The bore defined by the wall surface can be coaxial with a centerline of the lead 70 or can be offset from the center line.

The lead 70 can include one or more electrodes 72 through which an electrical current can be passed to stimulate the patient 40. A current carrying lead or wire 74 can be used to carry a current to the electrode 72 on the lead 70. The wire 74 can be integrated into the lead 70 and connect with the electrodes 72 of the lead 70. The lead 70 can be any appropriate lead, such as the Pisces® or Pisces-Quad® medical apparatuses sold by Medtronic, Inc. having a place of business in Minneapolis, Minn., USA. The lead 70 can have a selected number of electrodes, such as 4, 8, 12, etc.

The connecting wires 74 can be connected to a selected system, such as a neurostimulator. The neurostimulator can be incorporated into the EM controller 22 or provided as a separate device. The lead 70 can be positioned over the stylet 30, such as over the proximal end 52 of the stylet 30 to be positioned in the patient 40, as discussed further herein.

Figure 3B:
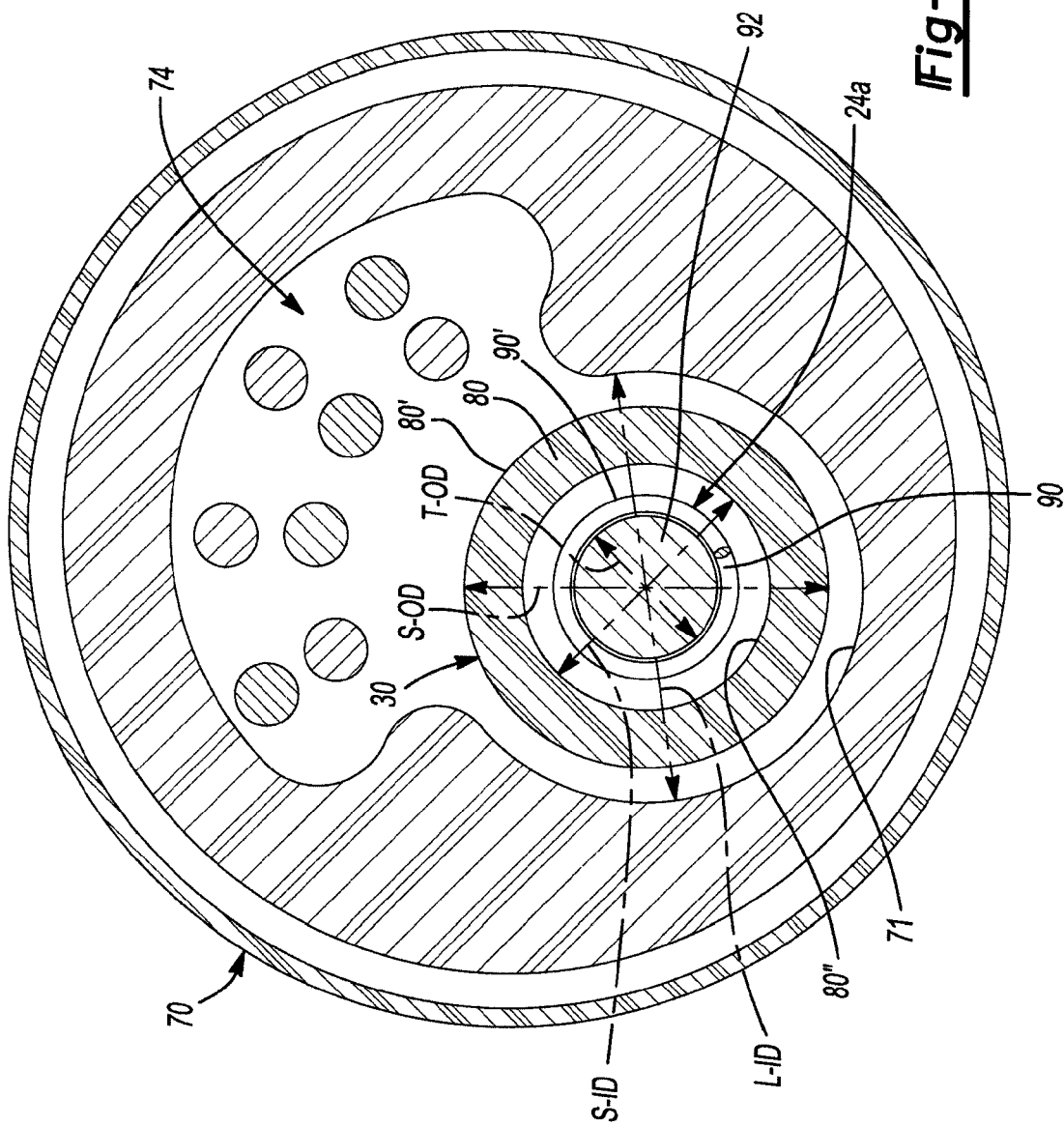
FIG. 3B is a cross-sectional view of a stylet, lead, and tracking device.

With continuing reference to FIG. 2B and additional reference to FIGS. 3A and 3B, the stylet 30 can be formed by the tube or hypo tube 50 that has a wall 80 that has an external wall surface 80' and an internal wall surface 80". The external wall surface 80' defines a style outer diameter (S-OD). The OD of the stylet 30 can be about 0.2 mm to about 0.7 mm, including about 0.01 inches (in) (about 0.25 millimeters (mm)to about 0.025 in (about 0.6 mm). It will be understood, however, that the OD of the stylet 30 can be any appropriate OD and can be provided to fit within an internal volume of the lead 70. The inner wall surface 80" of the stylet 30 defines a stylet inner diameter (S-ID). The lead 70 can have the inner wall surface 71 that defines a lead inner diameter (L-ID), such as about 0.3 mm to about 0.8 mm, including about 0.015 in (about 0.38 about) to about 0.030 (about 0.76 mm). An appropriate clearance between the OD of the stylet 30 and the ID of the lead 70 can be provided.

The stylet wall 80 can be any appropriate thickness formed of appropriate materials to provide a selected rigidity of the stylet 30. The wall 80 of the stylet 30 can be formed of stainless steel. This material can allow the stylet 30 to be rigid enough to move the lead 70 through the patient 40. As discussed further herein, a stylet 30 can be used to drive or move the lead 70 into the patient 40. Accordingly, the stylet 30 can be formed of an appropriate rigidity and toughness to allow for force to be transmitted to the lead 70 to push the lead into the patient 40.

The tracking devices 24a, 24b, 24c can be positioned within the bore defined within the stylet 30 at selected locations. The tracking devices 24a-24c can be positioned in the stylet 30 by moving the tracking devices 24a-24c into the stylet 30 from the proximal end 54 towards the distal end 52. The distal end 52 can be capped with an adhesive or physical barrier cap 82. The tracking devices 24a-24c can be fixed within the stylet 30 with appropriate mechanisms, such as an adhesive 95 applied on an exterior of the tracking devices 24a-24c and allowed to setup once the tracking devices 24a-24c are positioned within the stylet 30.

As discussed above, the distal end of the stylet 52 can include an angled tip portion 58. The tip portion 58 can be angled at an appropriate angle α relative to the remaining portion of the stylet 30. The angle α can be defined as an angle between a long body axis 85a of the stylet body 85 and a long axis 58a of the angle tip portion 58 distal of the curved region 84. The radius of the curved portion 84 can be an appropriate radius, including those discussed above. The radius of the curved portion 84, however, can be about one half inch (12 mm) to form the angle α to be about 20 degrees to about 35 degrees.

Different regions of the stylet 30 are defined, as discussed above. A first distance D1 can be formed between a very distal tip of the tip portion 58 and a proximal region of the curved portion 84. The distance D1 can be any appropriate distance, such as about one third of an inch. A second distance D2 can be a distance that is defined as the distance from the end of the stylet 30 to the second tracking device 24b. The distance of D2 can be any distance, such as about one half inch. Finally, a distance D3 can be defined from the distal tip of the stylet 30 to the third tracking device 24c. The third tracking device 24c can be positioned at a selected distance, such as about two or three inches, from the distal end of the stylet 30. The positions of the tracking devices 24a-24c can be selected for use with the lead 70. For example, the first tracking device 24a can be positioned at or near the distal tip of the stylet 30 to allow for discreet tracking of the distal tip. The second tracking device 24b can be positioned just proximal of the curved portion 84 to allow discreet tracking of the stylet body. Finally, the third tracking device 24c can be positioned to allow for discreet tracking of an end, such as the proximal end, of the lead 70. Alternatively, if a most proximal electrode 72p is inbound of a proximal end 70p of the lead 70 then the third tracking device can be positioned to allow discreet tracking of the proximal electrode 72p.

The third tracking device 24c can be positioned at a distance from the distal tip 52 of the stylet 30 that is substantially equivalent with the proximal electrode 72p or proximal portion (e.g. terminal end) of the lead 70 that is positioned with the stylet 30. That is, as illustrated in FIG. 2B, the proximal electrode 72p of the lead 70 can overlap or be positioned at or over a portion of the third tracking device 24c. Accordingly, as discussed further herein, by determining the position of the third tracking device 24c, the proximal most electrode 72p or end portion of the lead 70 can also be determined.

With reference to FIGS. 3A and 3B, the tracking devices 24a-24c can be positioned within the stylet 30 by being positioned within an internal stylet volume defined by the wall 80 of the stylet tube 50. The tracking device 24a, for example as illustrated relative to the first end, can be formed by providing a coil of a plurality of windings of a wire 90 (or other appropriate conductive material) around an appropriate core material or core 92. The wire windings 90 can be formed of an appropriate metal wire or conductive material, such as copper wire. The wire 90 can be a selected diameter including about 0.01 mm to about 0.02 mm, including about 0.0004 inches (about 0.0102 mm). Also, more than one coil of the wire can be positioned with the single tracking device to allow for multiple degree of freedom of position and orientation information per tracking device.

The wire 90 of the tracking devices 24a-c can be insulated wire. Alternatively, or in addition to the insulated wire a secondary material 95 can be positioned around one or more of the tracking devices 24a-c. The secondary material 95 can define at least two items: 1) an adhesive that is used to fix the tracking devices 24a-c inside the stylet 30 or 2) a heat shrink or varnish is used to protect tracking devices 24a-c during handling and assembly of the tracking devices 24a-c within the stylet 30.

The core 92 can be any appropriate material, such as a high magnetic permeability material, which can include metal alloys. An exemplary high permeability metal includes MUMETAL® sold by MAGNETIC SHIELD CORPORATION, having a place of business in Illinois, USA. A tracking device conductor or connector 94 extends from each of the tracking devices 24a-24c to communicate with the EM controller 22 through the connector 62. Although, as discussed above, the tracking devices 24a-24c can be configured in a wireless manner, they are illustrated with a wired configuration where the connector wires 94 can pass through the inner diameter of the stylet 30 to the connector 62.

With reference to FIG. 3B, the lead 70 includes an internal wall or surface 71 that defines the ID. The stylet 30 has the wall 80 that has the outer surface 80' that defines the S-OD of the stylet 30. The wall 80 further defines the internal wall surface 80" that defines the S-ID of the stylet 30. The tracking device 24a has the windings 90 that define an outer surface 90' that defines a tracking device outer diameter T-OD. As illustrated in FIG. 3B, appropriate tolerance distances can be defined between each of the lead 70, stylet 30, and tracking devices 24a-c. The tolerances can be formed to allow for an appropriate manipulation of the lead 70 within the patient 40. Substantially tight tolerances, such as about 0.02 mm to about 0.2 mm, including about 0.001 inches (about 0.025 mm) to about 0.004 inches (about 0.102 mm), can be provided between each of the components. The tolerances can allow for fixation of the tracking devices 24a-c within the stylet 30 and for appropriate manipulation and tight manipulation of the lead 70 with the stylet 30. Maintaining the tracking devices 24a-24c within the stylet 30, along with all of the connecting wires 94, can eliminate interference or "snagging" of any of the tracking devices 24a-24c or the connector wires 94 with other portions, such as the internal wall surface 71 of the lead 70.

Figure 4B:
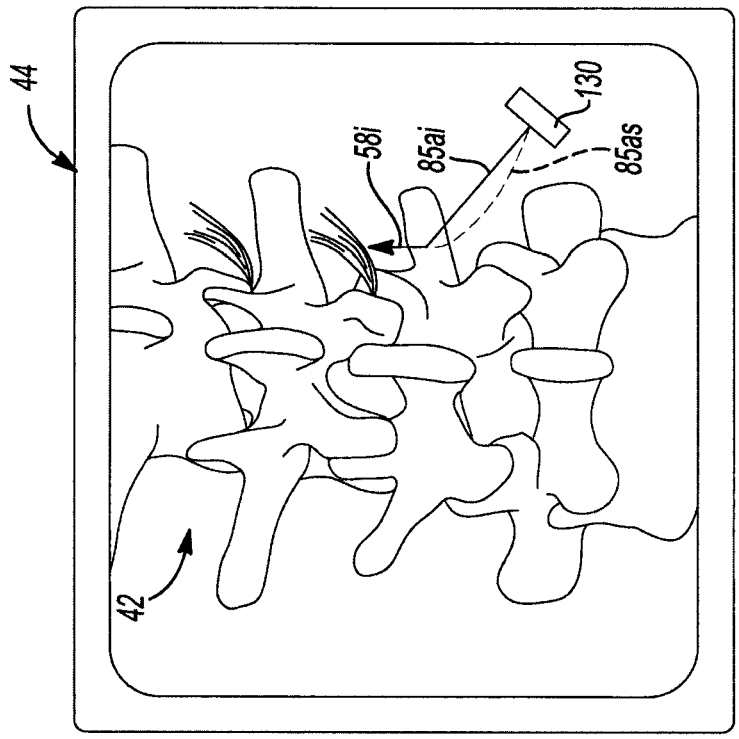
FIG. 4B is a schematic view of a display device with image data and icons representing locations of instruments.
Figure 4A:
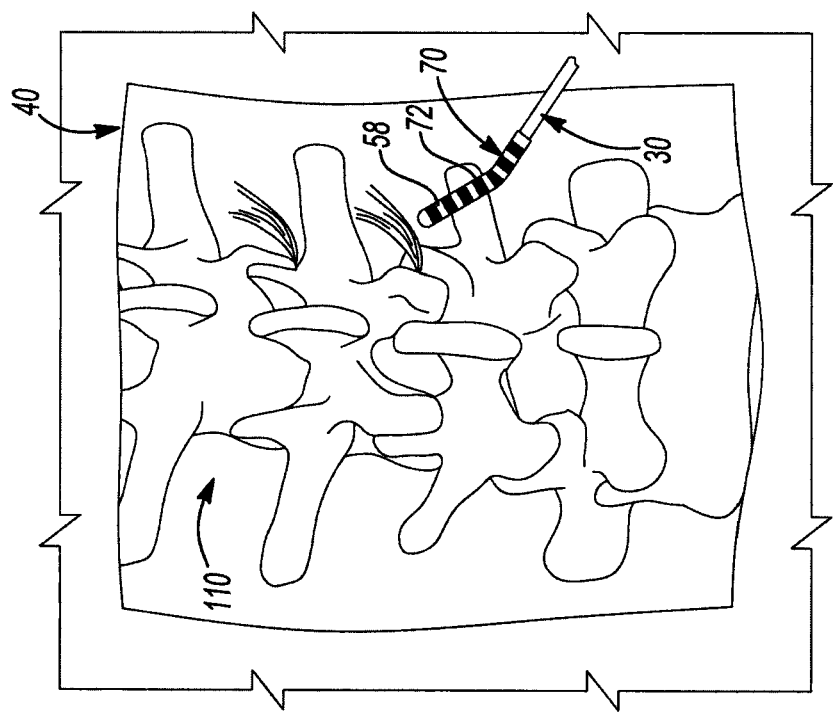
FIG. 4A is a schematic environmental view of an instrument and a patient.

As discussed above, each of the tracking devices 24a-24c can be tracked with the tracking system 12 that can include the electromagnetic tracking system 12. In an exemplary use, as illustrated in FIG. 4A, the stylet 30 can be positioned near a spinal column or spinal region 110 of the patient 40. The EM localizer 20 can generate a field near the spinal region 110 that encompasses the volume of the spinal column 110 that is appropriate for a selected procedure. The tracking devices 24a-24c can cooperate or sense the field and a signal can be generated that is used to determine or track a location of each of the tracking devices 24a-24c. Because each of the tracking devices are connected with the tracking system separately, each can be used to determine a unique location in the subject space for use by the navigation system 10, such as for display on the display device 44. As is understood and discussed above, the image 42 on the display device 44 is registered to the patient space of the patient 40 and can be used to illustrate one or more icons representing information regarding the stylet 30, the lead 70, or each of the tracking devices 24a-24c.

Because the stylet 30 is formed to include a selected rigidity, the tip portion 58 is angled relative to the remaining portion of the stylet 30 and the first tracking device 24a positioned within the tip 58 can be used to determine the position of the tip portion 58 relative to the remaining portion of the stylet 30. Accordingly, the axis 58a defined by the tip portion 58 can be determined and illustrated as a first icon or icon portion 58i, as illustrated in FIG. 4B. The icon 58i can include a line and an arrow point to indicate direction or orientation of the tip portion 58 towards the most distal end of the stylet 30.

In addition, the stylet 30 may flex during use. The three tracking device 24a-c can allow for the discrete and accurate tracking of three points of the stylet 30. This allows the navigation system 10 to define the position of the stylet 30 more accurately with three points on the display device 44. Accordingly, in addition to illustrating the vectors and lines, the display device 44 may also display a curve or spline icon 85as that illustrates a curve as an estimation of the position of the entire length of the lead 70 within the patient 40.

Generally, the tracking devices can resolve at least five degrees of freedom position information regarding the position of the tracking device 24a-24c in subject space. Accordingly, both an alignment or orientation and a X, Y, and Z coordinate location can be determined for each of the tracking devices 24a-24c. The five degrees of freedom allow the second tracking device 24b to be used to determine a position of the stylet 30 that is proximal to the curved portion 84 to determine the position of the tip portion 58 relative to the remaining portion of the stylet body 85.

The third tracking device 24c can be used, however, to further refine or more accurately determine the long axis 85a of the stylet body 85. Each of the second and third tracking devices 24b,c can be tracked and the axis 85a can be determined between them. The line between the second and third tracking devices 24b,c can define the long axis 85a of the stylet body 85 relative to the axis 58a of the tip portion 58. The long axis 85a can be illustrated as a second icon or icon portion 85ai on the display 44.

During a procedure, as illustrated in FIG. 4A, the lead 70 can be positioned over the stylet 30 and the user 60 can push the stylet 30 to move the lead 70 into the patient 40. The tip portion 58 of the stylet 30 forms a similar angle in the lead 70 as the lead 70 is moved into the patient 40. Due to the physical interaction of the tissues of the patient 40 and the exterior surface of the lead 70, the force of axially pushing along the stylet 30 will move the lead 70 along the axis 58a of the stylet 30. Accordingly, the stylet 30 that includes an tip portion 58 can be used to steer or move the lead 70 in a selected location. The axis 58a defines the general direction or range of movement of the lead 70 once the lead and stylet are positioned within the patient 40.

The position of each of the tracking devices 24a-24c that are tracked and determined within the navigation system 10 can be illustrated on the display device 42. Each of the locations of the tracking devices 24a-24c can be illustrated individually or macro-information, such as the position or angle of the tip portion axis 58a of the tip portion 58 relative to the long body axis 85a of the stylet body 85 can be illustrated. The tip portion axis 58a can be illustrated on the display 44 with the icon 58i to illustrate a location or direction that the lead 70 will move if the stylet 30 is pushed while the stylet 30 is in its current orientation relative to the patient 40. The arrow head can assist in the visualization of projected movement of the lead 70. As discussed above, due to the tip portion 58 pushing the stylet 30 will cause the stylet 30 and lead 70 to move in the direction defined by the axis 58a of the tip portion 58.

To assist with lead placement and display, as illustrated in FIG. 2B, the lead 70 can have a length that substantially extends from the distal tip 52 of the stylet 30 to the position of the third tracking device 24c. By positioning the third tracking device 24c substantially at a position within the stylet 30 that is equivalent with an end 70a of the lead 70, tracking the position of the tracking device 24c can also be used to determine the end position 70a of the lead 70, substantially simultaneously. The lead 70, as discussed above, includes one or more electrodes 72 positioned along an exterior of the lead 70. Accordingly, determining the location of the selected electrodes 72 on the lead 70 during a positioning of the lead 70 within the patient 40 can be useful in confirming or selecting a location for positioning the lead 70 within the patient 40. A third icon or icon portion 130 can be used to illustrate the location of the end of the lead 70 on the display device 44.

It will be understood that the lead 70, however, can be provided in a plurality of lengths. Accordingly, the stylet 30 can include a plurality of stylets each including tracking devices positioned at different positions within the stylet 30. A lead with a first selected length can be associated or positioned within the patient 40 with a first stylet and a lead with a different length can be positioned with a different stylet in the patient 40. Regardless of the length of the lead, however, the position of the third tracking device 24c can be used to determine the position of the lead 70 within the patient 40 by being substantially positioned at an end of the lead 70.

The plurality of tracking devices 24a-c positioned in the stylet 30 can also be used to enhance or increase accuracy of determination of the position of the stylet 30, including the location of the tip portion 58. The first tracking device 24a positioned within the tip portion 58 can be used to determine the position of the tip portion 58. The second tracking device 24b, that is also positioned in the stylet 30, can be positioned proximal to the curved portion 84. As discussed above, each of the tracking devices 24a-24c can be used to determine both orientation and location to identify a position of the respective tracking devices 24a-24c. Thus, the second tracking device 24b can be used to determine a position of the stylet body 85 relative to the tip portion 58 because the second tracking device 24b is positioned within a portion of the stylet 30 that is not a portion of the tip portion 58. The third tracking device 24c can be used to enhance accuracy of determining the position or axis 85a of the stylet body 85 that does not form the tip portion 58.

The third tracking device 24c can also be used with the second tracking device 24b to together define two points in the subject space that can be used to calculate the axis 85a of the stylet body 85. These two points enhance accuracy by allowing for calculation of reduced error of the axis 85a to the stylet 30 by calculating the position of both of the tracking devices 24b and 24c. Regardless, the position of the tip portion 58 can be further determined relative to the axis 85a defined by the two tracking devices 24b and 24c for determining a position of the tip portion 58 to further determine a direction of movement of the lead 70 if pushed with the stylet 30.

Additionally, the third tracking device 24c can be used to determine or account for flex in the stylet 30. Although the stylet 30 is selected to be substantially rigid, the stylet 30 may flex over a selected distance. Accordingly, the lead 70 that is positioned over the stylet 30 that extends between the second tracking device 24b and the third tracking device 24c can also flex or be substantially non-linear over the distance that the stylet 30 flexes. A position of the third tracking device 24c can be used to assist in determining whether flex is occurring in the stylet 30. It will also be understood, however, that an appropriate amount of flex can be accounted for and be used during the navigation of the lead 70 into the patient 40 and the third tracking device 24c can simply be used to identify the amount of flex.

The stylet 30, including the three tracking devices 24a-24c within the wall 80 of the tube can be used to position the lead 70 within the patient 40. As discussed above, the tolerances between the external diameter or outer diameter of the stylet 30 and the inner diameter of the lead 70 can be made substantially small by positioning all of the connections and the tracking devices 24a-24c within an inner diameter of the stylet 30. By positioning the tracking devices 24a-24c and the connector wires 92 within the wall 80 of the stylet 30 a chance of snagging or damaging the tracking devices 24a-24c, the connector wires 92, or any of the other portions of the tracking devices 24a-24c is substantially eliminated. This can also allow for reusability of the stylet 30 with the tracking devices 24a-c because they are protected within the stylet 30 from damage and deleterious affects from an external environment.

In addition, the tracking devices 24a-24c can be optimized and manufactured separately from the stylet 30 and assembled efficiently for use. This can allow the stylet 30 and the associated tracking devices to be designed for different applications and optimized separately. Once assembled, the tracking devices 24a-24c can be calibrated within the stylet 30 for precisely determining the position of the tracking devices 24a-24c when used with the stylet 30.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A lead placement system for placing a lead in a subject, the lead placement system comprising:
   the lead;
   a stylet comprising a body, a curved portion and an angled portion, wherein
      the stylet is tubular shaped,
      the body extends along a first axis between a proximal end of the stylet and the curved portion,
      the angled portion extends along a second axis from the curved portion to a distal end of the stylet, and
      the second axis is at a fixed predetermined angle relative to the first axis;
   a first tracking device disposed within the angled portion;
   a second tracking device disposed (i) within the stylet, (ii) within or proximal the curved portion, and (iii) proximal to the first tracking device,
   wherein the stylet is configured to be inserted in and extend along at least a portion of the lead; and
   a plurality of electrodes (i) configured to supply an electrical current to the subject to stimulate the subject, and (ii) disposed on the lead and surrounding portions of at least one of the angled portion, the curved portion and the body,
   wherein
      the lead has an inner diameter and an outer diameter,
      each of the plurality of electrodes has an inner diameter and an outer diameter, and
      at least one of (i) the inner diameter of each of the plurality of electrodes is equal to the inner diameter of the lead, or (ii) the outer diameter of each of the plurality of electrodes is equal to the outer diameter of the lead.

2. The lead placement system of claim 1, further comprising a third tracking device disposed within the body and proximal to the second tracking device,
   wherein the second tracking device and the third tracking device are configured to define the first axis relative to the second axis.

3. The lead placement system of claim 2, further comprising:
   the lead; and
   an electrode,
   wherein at least a portion of the third tracking device is disposed within a volume surrounded by the electrode when the stylet is within the lead.

4. The lead placement system of claim 3, further comprising at least one processor comprising hardware configured to:
   track locations of the first tracking device, the second tracking device, and the third tracking device; and
   based on the locations, determine a direction of the angled portion relative to the body.

5. The lead placement system of claim 4, further comprising a display device operable to display:
   at least one icon representing at least one of the first tracking device, the second tracking device, the third tracking device, and the lead; and
   a second icon representing the orientation of the angled portion relative to the body.

6. The lead placement system of claim 2, wherein:
   the first tracking device, the second tracking device, and the third tracking device are at predetermined fixed positions within the stylet;
   the stylet has an inner diameter; and
   the first tracking device, the second tracking device, and the third tracking device are all disposed within the stylet.

7. The lead placement system of claim 6, wherein the first tracking device, the second tracking device, or the third tracking device is adhered within the stylet with an adhesive.

8. The lead placement system of claim 1, further comprising:
   a third tracking device disposed within the stylet and proximal to the second tracking device;
   a processor comprising hardware configured to determine locations of the first tracking device, the second tracking device, and the third tracking device; and
   a display device operable to display an image and an icon, wherein the icon represents a location of (i) at least a portion of the stylet, (ii) the lead, or (iii) the at least the portion of the stylet and the lead.

9. The lead placement system of claim 8, wherein:
   the stylet includes an outer diameter;
   the lead has an inner diameter; and
   a clearance between the outer diameter of the stylet and the inner diameter of the lead is about 0.01 mm to about 0.02 mm.

10. The lead placement system of claim 8, wherein the predetermined angle between the first axis and the second axis is 25-35 degrees.

11. The lead placement system of claim 8, further comprising a localizer configured to generate an electromagnetic field, wherein:
each of the first tracking device, the second tracking device, and the third tracking device include a respective coil; and
the coils are operable to sense the electromagnetic field generated by the localizer.

12. The lead placement system of claim 11, wherein each of the first tracking device, the second tracking device and the third tracking device includes a respective plurality of coils.

13. The lead placement system of claim 11, wherein:
each of the first tracking device, the second tracking device, and the third tracking device includes a respective coil; and
each of the coils is formed around a respective elongated magnetic permeable core.

14. The lead placement system of claim 8, wherein the hardware of the processor is configured to, based on tracking information, determine a target location of the icon relative to the image.

15. The lead placement system of claim 1, wherein:
the plurality of electrodes include a first electrode, a second electrode, and a third electrode;
the first electrode surrounds a portion of the angled portion;
the second electrode surrounds a portion of the curved portion; and
the third electrode surrounds a portion of the body.

16. The lead placement system of claim 1, wherein:
the inner diameter of each of the plurality of electrodes is equal to the inner diameter of the lead; and
the outer diameter of each of the plurality of electrodes is equal to the outer diameter of the lead.

17. The lead placement system of claim 1, further comprising a plurality of wires connected to respective ones of the plurality of electrodes and extending (i) along and within the lead, and (ii) along and external to the stylet.

18. The lead placement system of claim 1, wherein the body and the angled portion are straight members of the stylet.

19. The lead placement system of claim 1, wherein the stylet extends from a proximal end of the lead to a distal end of the lead.

20. The lead placement system of claim 1, wherein the plurality of electrodes surround portions of the angled portion, the curved portion and the body.

21. The lead placement system of claim 1, wherein the second tracking device is disposed within the curved portion.

22. The lead placement system of claim 1, wherein the second tracking device is disposed adjacent to the curved portion.

23. The lead placement system of claim 17, wherein:
the lead comprises an internal channel;
the internal channel extends along and is external and adjacent to the stylet; and
the plurality of wires are disposed within and extend along the internal channel.

24. The lead placement system of claim 23, wherein:
the lead comprises a first internal volume and a second internal volume;
the stylet is disposed in the first internal volume;
an outer diameter of the stylet corresponds to a diameter of the first internal volume;
the plurality of wires are disposed in the second internal volume; and
the second internal volume is defined by the internal channel.

25. The lead placement system of claim 24, wherein:
a thickness of a wall of the lead varies along an inner perimeter of the lead; and
the thickness of the wall is thickest at points along the inner perimeter of the lead and adjacent to both the first internal volume and the second internal volume.

26. A method of placing a lead in a subject, the method comprising:
positioning a stylet within the lead, wherein the lead has a plurality of electrodes on the lead, wherein the lead has an inner diameter and an outer diameter, wherein each of the plurality of electrodes has an inner diameter and an outer diameter, and wherein at least one of (i) the inner diameter of the plurality of electrodes is equal to the inner diameter of the lead, or (ii) the outer diameter of the plurality of electrodes is equal to the outer diameter of the lead;
holding the stylet in a fixed relationship with the lead such that the lead moves with the stylet, wherein
the stylet comprises a body, a curved portion and an angled portion, wherein the stylet is tubular shaped,
the plurality of electrodes surround portions of at least one of the angled portion, the curved portion and the body,
the body is proximal to the curved portion and extends along a first axis between a proximal end of the stylet and the curved portion,
the angled portion is distal to the curved portion and extends along a second axis from the curved portion to a distal end of the stylet, and
the second axis is at a fixed predetermined angle relative to the first axis;
tracking a first tracking device disposed within the angled portion;
tracking a second tracking device disposed within the stylet;
displaying an icon representing a position of at least one of the stylet and the lead; and
supplying an electrical current via the plurality of electrodes to the subject to stimulate the subject.

27. The method of claim 26, further comprising:
displaying a location of one of the plurality of electrodes; and
tracking a third tracking device disposed within the stylet and proximal to the second tracking device,
wherein at least a portion of the third tracking device is located within a volume surrounded by the one of the plurality of electrodes.

28. The method of claim 26, wherein:
the stylet is configured to be moved along a path that is defined by the angled portion relative to the body; and
the angled portion is at the distal end of the stylet and interacts with the subject to direct movement of the lead and stylet within the subject.

29. The method of claim 26, further comprising adhering the first tracking device and the second tracking device within the stylet.

30. The method of claim 26, wherein the tracking of the first tracking device and the tracking of the second tracking device includes:
generating an electromagnetic field within the subject;
sensing the electromagnetic field with the first tracking device and the second tracking device; and
determining positions of the first tracking device and the second tracking device within the electromagnetic field.

* * * * *